United States Patent
Eskesen et al.

(10) Patent No.: US 11,306,048 B2
(45) Date of Patent: Apr. 19, 2022

(54) PROCESS AND A PLANT FOR THE PRODUCTION OF METHANOL

(71) Applicant: HALDOR TOPSØE A/S, Kgs. Lyngby (DK)

(72) Inventors: Søren Grønborg Eskesen, Espergærde (DK); Per Juul Dahl, Vedbæk (DK); Emil Andreas Tjärnehov, Limhamn (SE); Max Thorhauge, Herlev (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 17/055,284

(22) PCT Filed: Jun. 11, 2019

(86) PCT No.: PCT/EP2019/065133
§ 371 (c)(1),
(2) Date: Nov. 13, 2020

(87) PCT Pub. No.: WO2019/238635
PCT Pub. Date: Dec. 19, 2019

(65) Prior Publication Data
US 2021/0188747 A1 Jun. 24, 2021

(30) Foreign Application Priority Data
Jun. 12, 2018 (DK) .................... PA 2018 00267

(51) Int. Cl.
*C07C 29/154* (2006.01)
*B01J 19/00* (2006.01)
(Continued)

(52) U.S. Cl.
CPC .......... *C07C 29/154* (2013.01); *B01J 19/002* (2013.01); *B01J 23/80* (2013.01); *C07C 29/152* (2013.01);
(Continued)

(58) Field of Classification Search
CPC ... C07C 29/154; C07C 29/152; C07C 29/151; C07C 31/04; B01J 19/002; B01J 23/80;
(Continued)

(56) References Cited

U.S. PATENT DOCUMENTS

| 3,897,471 | A | 7/1975 | Herbert et al. |
| 5,631,302 | A | 5/1997 | Koenig et al. |

(Continued)

FOREIGN PATENT DOCUMENTS

| WO | 2014012601 A1 | 1/2014 |
| WO | 2014095978 A2 | 6/2014 |

(Continued)

OTHER PUBLICATIONS

Danish Search Report dated Nov. 29, 2018, issued in corresponding Danish Patent Application No. PA 2018 00267. (8 pages).
(Continued)

*Primary Examiner* — Jafar F Parsa
(74) *Attorney, Agent, or Firm* — Buchanan Ingersoll & Rooney P.C.

(57) ABSTRACT

A process for the production of methanol from synthesis gas via an equilibrium reaction is conducted in a methanol pre-converter within a certain operational window, said operational window being defined by the area below an approximately linear curve of the partial pressure of carbon monoxide vs. the boiling water temperature for water temperatures between 210 and 270° C. Methanol of different product grades may be obtained by operating in specific areas of the operational window.

6 Claims, 3 Drawing Sheets

(51) Int. Cl.
    *B01J 23/80* (2006.01)
    *C07C 29/152* (2006.01)
(52) U.S. Cl.
    CPC .............. *B01J 2219/00054* (2013.01); *B01J 2219/00162* (2013.01)
(58) Field of Classification Search
    CPC . B01J 2219/00162; B01J 8/0285; B01J 8/001
    See application file for complete search history.

(56) References Cited

U.S. PATENT DOCUMENTS

| | | |
|---|---|---|
| 2007/0293590 A1 | 12/2007 | Hipp |
| 2018/0237366 A1 | 8/2018 | Modarresi |
| 2019/0126231 A1 | 5/2019 | Modarresi |

FOREIGN PATENT DOCUMENTS

| | | |
|---|---|---|
| WO | 2015193440 A1 | 12/2015 |
| WO | 2017025272 A1 | 2/2017 |
| WO | 2017121981 A1 | 7/2017 |
| WO | 2017167642 A1 | 10/2017 |

OTHER PUBLICATIONS

International Search Report (PCT/ISA/210) dated Sep. 19, 2019, by the European Patent Office as the International Searching Authority for International Application No. PCT/EP2019/065133.
Written Opinion (PCT/ISA/237) dated Sep. 19, 2019, by the European Patent Office as the International Searching Authority for International Application No. PCT/EP2019/065133.

PROCESS AND A PLANT FOR THE PRODUCTION OF METHANOL

TECHNICAL FIELD

The present invention concerns a process and a plant for the production of methanol. The invention especially has its focus on the operation of methanol reactors. More specifically, the main focus is on the operational window in methanol reactors.

BACKGROUND AND SUMMARY

Methods for the production of methanol by catalytic conversion of synthesis gas containing hydrogen and carbon oxides have been known for a long time to persons skilled in the art. Thus, methanol is mainly produced catalytically from a mixture of carbon monoxide, carbon dioxide and hydrogen, i.e. methanol synthesis gas, under high pressure and temperature, most often using a copper-zinc oxide-alumina ($Cu/ZnO/Al_2O_3$) catalyst.

Methanol is produced from the synthesis gas (syngas) via an equilibrium reaction, which proceeds at elevated temperature under elevated pressure. The synthesis reactions are:

$$CO + 2H_2 \leftrightarrow CH_3OH + heat \qquad (1)$$

$$CO_2 + 3H_2 \leftrightarrow CH_3OH + H_2O + heat \qquad (2)$$

$$CO + H_2O \leftrightarrow CO_2 + H_2 + heat \qquad (3)$$

Since reactions (1) to (3) are exothermic, the chemical equilibrium constants decrease with increasing temperature. Therefore, low reactor temperatures should improve conversion, provided they are not so low that the specific reaction rates are too small. For a given reactor size and a specific desired conversion, the recycle flow rate increases as reactor temperatures are lowered, which means higher compressor work.

It has turned out that it is advantageous to operate the methanol synthesis reactions in an operational window that is limited by a curve describing the relationship between the partial pressure of CO and the reactor temperature. More specifically, operating within certain combinations of partial CO pressure and temperature will lead to a fast deactivation of the catalyst. This goes for any layout around the methanol reactor, such as the methanol loop with or without pre-converter and irrespective of the layout being a novel design or a revamp.

Depending on the specific combination of the partial pressure of CO and the boiling water temperature, different methanol grades, such as grade AA methanol or fuel grade methanol, can be obtained within the operational window.

A typical methanol plant operated with a natural gas feed is divided into three main sections. In the first part of the plant, natural gas is converted into syngas. The syngas reacts to produce methanol in the second section, and then methanol is purified to the desired purity in the tail-end of the plant. In a standard synthesis loop, a methanol reactor, most often a boiling-water reactor (BWR), is used to convert a mixture of synthesis gas from a reformer/gasifier unit and recycle gas, i.e. unconverted synthesis gas, into methanol.

It has been found that a region of specific combinations of the partial CO pressure and the reactor temperature (in practice the boiling water temperature) can be established, within which it is considered "safe" to operate in the sense that advantageous results are obtained. More specifically, an approximately linear curve can be drawn for boiling water temperatures between 210° C. and 270° C. In this specific temperature range, the partial CO pressure corresponding to a given temperature displays an approximately linear increase from 20 kg/cm² at 210° C. to 32.5 kg/cm² at 270° C. The area below this curve defines the "safe" region of operation.

So the present invention concerns a process for the production of methanol from synthesis gas via an equilibrium reaction proceeding at elevated temperatures under elevated pressure according to the above synthesis reactions (1) to (3), said process being conducted in a methanol pre-converter within an operational window, said operational window being defined by the area below an approximately linear curve of the partial pressure of carbon monoxide vs. the boiling water temperature for water temperatures from 210 to 270° C., where the partial pressure of carbon monoxide increases from 20 kg/cm² at 210° C. to 32.5 kg/cm² at 270° C., and divided into two areas by an estimated bi-product curve of the partial pressure of carbon monoxide vs. the boiling water temperature, said areas leading to the production of methanol of different product qualities.

The process preferably is conducted in an area within the operational window to the left of and below the estimated by-product curve, which indicates the upper limit for obtaining grade AA methanol or methanol of similar quality. The estimated by-product curve is shown in FIG. 1 which identifies the operational window to be used in the process according to the invention.

It is well known in the art that a synthesis gas derived from natural gas or heavier hydrocarbons and coal is highly reactive for direct methanol synthesis and harmful for the catalyst. Moreover, use of such highly reactive synthesis gas results in formation of large amounts of by-products.

The reaction of carbon oxides and hydrogen to methanol is equilibrium-limited, and the conversion of the synthesis gas to methanol per pass through the methanol catalyst is relatively low, even when using a highly reactive synthesis gas.

Because of the low methanol production yield in a once-through conversion process, the general practice in the art is to recycle unconverted synthesis gas separated from the reaction effluent and dilute the fresh synthesis gas with the recycle gas.

This typically results in the so-called methanol synthesis loop with one or more reactors connected in series being operated on fresh synthesis gas diluted with recycled unconverted gas separated from the reactor effluents or on the reactor effluent containing methanol and unconverted synthesis gas. The recycle ratio (recycle gas to fresh synthesis feed gas) is from 2:1 up to 7:1 in normal practice.

When the methanol reactor in an existing methanol plant becomes the bottleneck in connection with capacity revamp projects, the standard solution is to install an extra reactor in series or in parallel or to modify the existing reactor. This is typically all done inside the loop. It has, however, turned out to be an advantage to install a once-through pre-converter between the make-up gas compressor and the methanol loop. This concept maintains the existing loop unchanged.

So, according to a preferred embodiment of the present invention, a once-through pre-converter is installed between the make-up gas compressor and the methanol loop, said pre-converter operating within the inventive operational window limited by a curve describing the relationship between the partial pressure of CO and the reactor temperature.

As regards prior art, Applicant's WO 2015/193440 A1 describes a process for producing methanol in reactors connected in series, where one of the aspects is to apply the process as part of a revamp, thereby providing a way to increase the production capacity of an existing methanol plant.

In Applicant's WO 2014/012601 A1, a reaction system for the preparation of methanol is described, which comprises two reaction units, of which the first unit is operated on a mixture of fresh synthesis gas and unconverted synthesis gas while the second unit is operated solely on unconverted synthesis gas.

U.S. Pat. No. 5,631,302 A describes production of methanol on copper-containing catalysts from a synthesis gas under a pressure from 20 to 120 bar at a temperature of 200-350° C. The synthesis gas is passed adiabatically through a first synthesis reactor containing a fixed bed of a copper-containing catalyst without any synthesis gas recycle. Together with recycle gas, the gas mixture which has not been reacted in the first synthesis reactor is passed through a second synthesis reactor, which contains a copper-containing catalyst disposed in tubes and indirectly cooled by boiling water.

In WO 2014/095978 A2, also belonging to the Applicant, a process for the production of higher ($C_{4+}$) alcohols is described, in which the alcohol synthesis gas is optionally first reacted in a heterogeneous alcohol pre-converter, whereby methanol is produced, and then the effluent from the pre-converter—or the synthesis gas in the absence of the pre-converting step—is reacted in a reactor for synthesis of higher alcohols.

In WO 2017/121981 A1, a methanol synthesis process is described, which comprises the steps of (i) passing a first synthesis gas mixture comprising a make-up gas through a first synthesis reactor to form a first product gas stream, (ii) recovering methanol from the first product gas stream, thereby forming a first methanol-depleted gas mixture, (iii) combining the first methanol-depleted gas mixture with a loop recycle stream to form a second synthesis gas mixture, (iv) passing the second synthesis gas mixture through a second synthesis reactor to form a second product gas stream, (v) recovering methanol from the second product gas stream, thereby forming a second methanol-depleted gas mixture, and (vi) using at least part of the second methanol-depleted gas mixture as the loop recycle gas stream. In this process, the first synthesis reactor has a higher heat transfer per $m^3$ of catalyst than the second synthesis reactor, and none of the loop recycle gas stream is fed to the first synthesis gas mixture, and the recycle ratio of the loop recycle gas stream to form the second synthesis gas mixture is in the range from 1.1:1 to 6:1. It is stated that the efficiency of multiple-stage methanol synthesis may be improved by using different recycle ratios for different types of reactor.

The best choice for the pre-converter to be used according to the invention is a boiling water reactor because of the very reactive synthesis gas. In order to limit the formation of by-products, a lower boiling water temperature in the pre-converter than in the existing reactor typically will be required, which in turn requires a separate steam drum.

The pre-converter concept according to the invention supplies the extra catalyst needed to process the extra make-up gas originating from upstream units. The pre-converter itself operates on fresh make-up gas. It is preferably of the boiling water reactor (BWR) type and will require an additional cooling system and possibly also individual cooling and separation of the condensed methanol from the pre-converter. The fresh make-up gas is very reactive towards by-product formation. A lower catalyst temperature therefore is foreseen compared to the existing reactor, hence the additional cooling system.

BRIEF DESCRIPTION OF THE DRAWINGS

The invention is described in more detail with reference to the figures, where.

DETAILED DESCRIPTION

Figure 1:
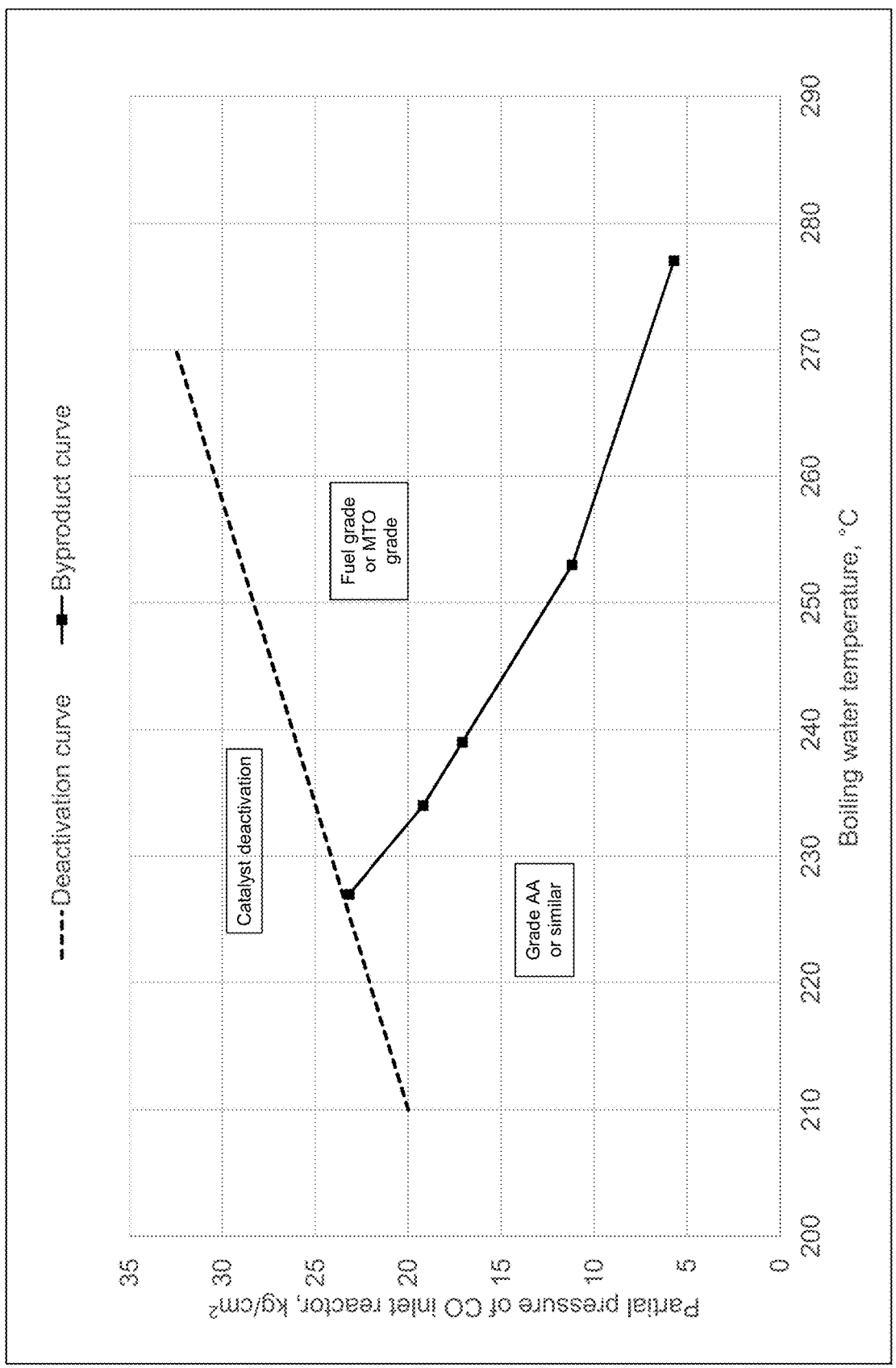
FIG. 1 shows the operational window to be used in the process according to the invention.

In FIG. 1, the operational window to be used in the process according to the invention is defined by the area below the approximately linear, dashed curve (the deactivation curve) of the partial pressure of carbon monoxide vs. the boiling water temperature for water temperatures from 210 to 270° C., where the partial pressure of carbon monoxide increases from 20 kg/cm$^2$ at 210° C. to 32.5 kg/cm$^2$ at 270° C.

As already mentioned, it is possible to obtain different methanol grades within the operational window depending on the combination of partial pressure of CO and boiling water temperature. In FIG. 1, the solid curve (the byproduct curve) indicates the upper limit for obtaining grade AA methanol or methanol of similar high quality. Operating above the curve will move the methanol product into a more byproduct-containing methanol product which is, however, pure enough to be counted as fuel grade or methanol-to-olefins (MTO) grade methanol.

Furthermore, the dashed deactivation curve depicts the limit for catalyst deactivation. Operating above the curve will lead to a fast deactivation of the catalyst.

Figure 2:
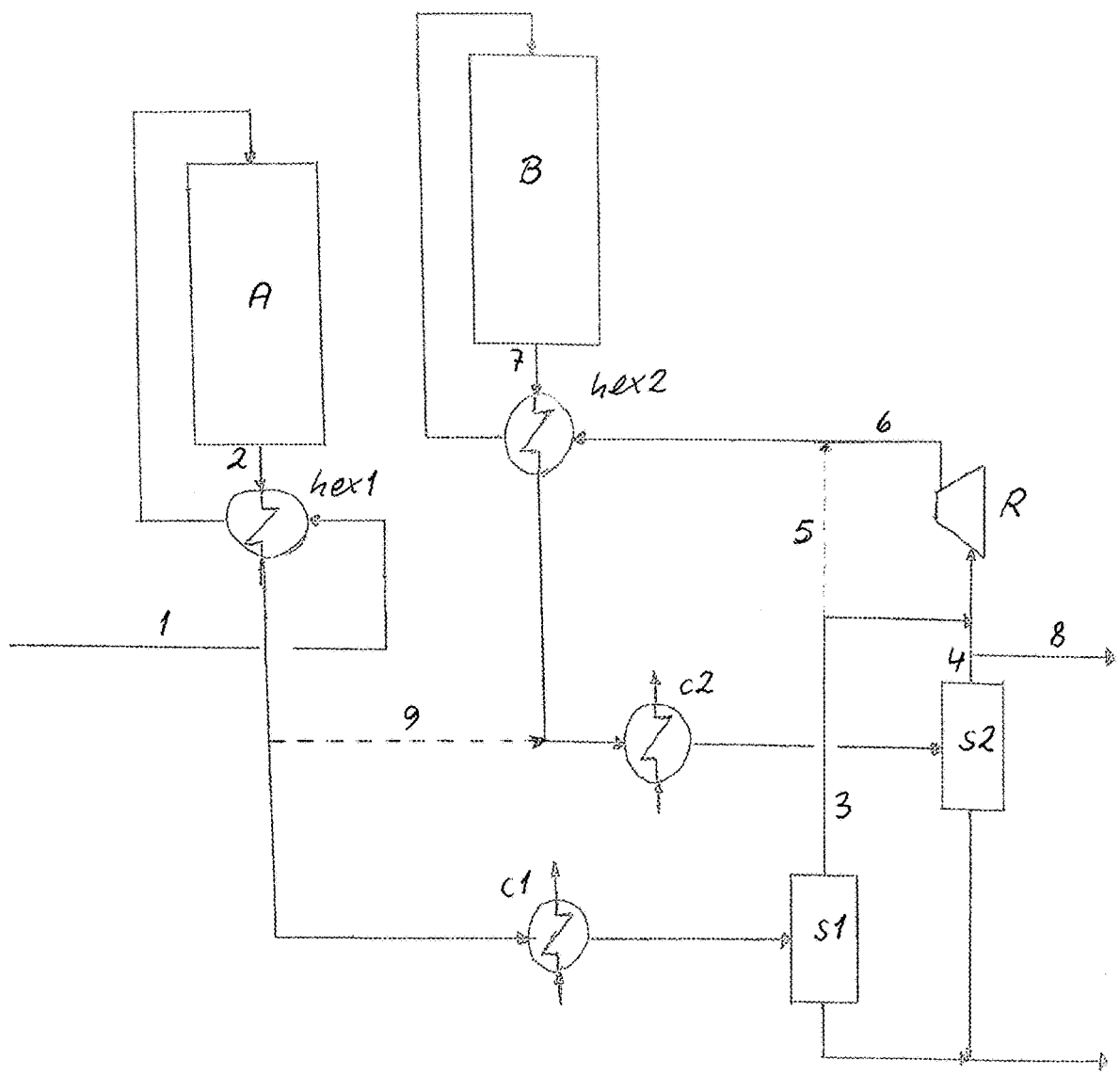
FIG. 2 shows an embodiment of the pre-converter concept according to the invention.

In FIG. 2, compressed make-up synthesis gas 1 (compressor not shown) is heated in the feed/effluent heat exchanger (hex1) before it enters the pre-converter (A). After being passed through the pre-converter, the gas 2 is cooled in the feed/effluent heat exchanger (hex1) and sent to a condenser c1, optionally sent to another condenser c2 as stream 9. As much as possible of the methanol is condensed in condenser c1 before the two-phase flow is separated in a first separator (s1). The gas 3 from the separator (s1) is then mixed with the gas 4 from a second separator (s2) or optionally sent directly downstream the recirculator (R) as stream 5.

After mixing, the gas is compressed in said recirculator (R). The resulting feed gas 6 to the reactor (B) is pre-heated in the feed/effluent heat exchanger (hex2) before it enters the reactor (B).

The outgoing gas 7 is cooled in the feed/effluent heat exchanger (hex2) prior to being cooled as much as possible in condenser c2 in order to condense as much methanol as possible. Then the two-phase flow is separated in the second separator (s2).

A small amount 8 of the gas from the separator (s2) is sent to purge to avoid build-up of inert constituents. The rest of the gas flow from the separator (s2) is mixed with the gas from the separator (s1). Finally, the liquids from the two separators (s1) and (s2) are mixed, and the mixture is sent to a low pressure separator before being sent out of the methanol section.

Figure 3:
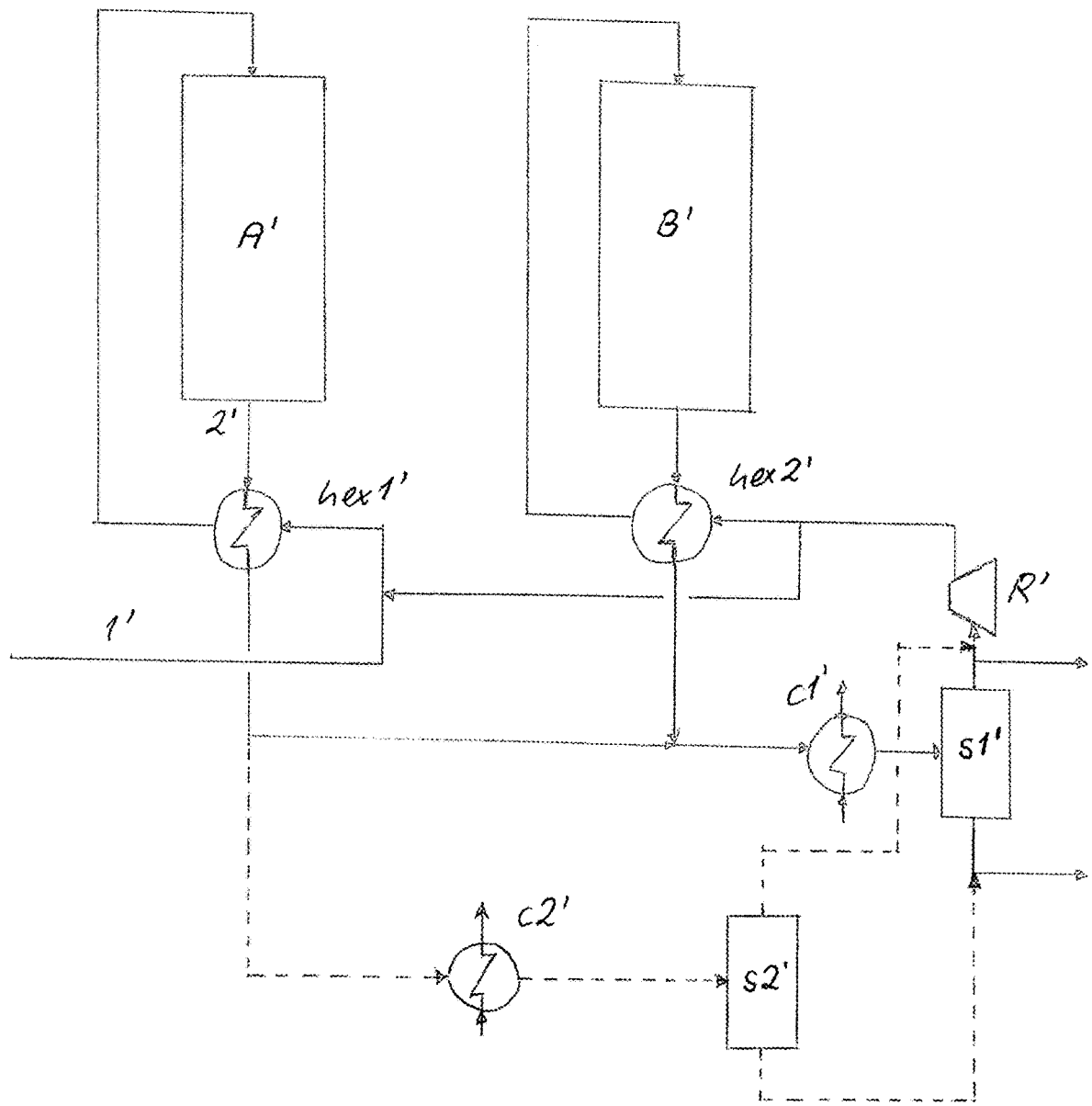
FIG. 3 shows an alternative embodiment of the pre-converter concept according to the invention.

FIG. 3 shows another embodiment, different from the one shown in FIG. 2. Here, the make-up synthesis gas (1') is compressed (compressor not shown), and the compressed gas is mixed with part of the recycled gas from the recirculator R' and heated in the feed/effluent heat exchanger (hex1') before it enters the pre-converter (A'). After passing through the pre-converter, the gas 2' is cooled in the feed/effluent heat exchanger (hex1'). Then the cooled gas from the pre-converter (A') is mixed with cooled gas from the reactor (B'). After the mixing, the two-phase flow is cooled further in condenser c1' to condense as much methanol as possible.

When the gas has cooled as much as possible, the two-phase flow is separated in a separator (s1'). Some of the outgoing gas from the separator is sent to purge to avoid build-up of inert constituents. The rest of the gas is sent to the recirculator R' and used as feed gas to the reactor (B'). The feed gas to reactor (B') is heated in the feed/effluent heat exchanger (hex2') before it enters the reactor. After reactor (B'), the gas is cooled in the feed/effluent heat exchanger (hex2') and mixed with cooled gas from the pre-converter (A').

Optionally, the cooled gas from the pre-converter (A') is fed to another condenser c2' to condense as much methanol as possible. After the gas has cooled, the two-phase flow is separated in another separator (s2'), from where the gas phase is sent to the inlet of the recirculator R', while the liquid phase is mixed with the liquid phase from separator s1'.

The fresh make-up gas is very reactive towards formation of by-products. A lower catalyst temperature compared to the existing reactor can therefore be foreseen; hence the additional cooling system.

The invention claimed is:

1. A process for the production of methanol from synthesis gas via an equilibrium reaction proceeding at elevated temperatures under elevated pressure according to the synthesis reactions $$CO+2H_2 \leftrightarrow CH_3OH+heat \quad (1)$$

$$CO_2+3H_2 \leftrightarrow CH_3OH+H_2O+heat \quad (2)$$

$$CO+H_2O \leftrightarrow CO_2+H_2+heat \quad (3)$$

in the presence of a catalyst, said process being conducted in a methanol pre-converter within an operational window, said operational window being
defined by the area below an approximately linear curve of the partial pressure of carbon monoxide vs. the boiling water temperature for water temperatures from 210 to 270° C., where the partial pressure of carbon monoxide increases from 20 kg/cm² at 210° C. to 32.5 kg/cm² at 270° C., and divided into two areas by an estimated by-product curve of the partial pressure of carbon monoxide vs. the boiling water temperature, said areas leading to the production of methanol of different product qualities.

2. Process according to claim 1, which is conducted in an area within the operational window to the left of and below the by-product curve, which indicates the upper limit for obtaining grade AA methanol or methanol of similar quality.

3. Process according to claim 1, which is conducted in an area within the operational window to the right of and above the by-product curve, where the methanol product is a more byproduct-containing methanol product which is still pure enough to be a fuel grade or methanol-to-olefins (MTO) grade methanol.

4. Process according to claim 1, wherein the catalyst is a Cu/ZnO-based catalyst.

5. A plant for the production of methanol by the process according to claim 1, said plant comprising a make-up gas compressor and a synthesis reactor in a methanol loop, wherein a once-through pre-converter is installed between the make-up gas compressor and the methanol loop, said pre-converter operating within the operational window defined by the area below the approximately linear, dashed curve of the partial pressure of carbon monoxide vs. the boiling water temperature for water temperatures from 210 to 270° C., where the partial pressure of carbon monoxide increases from 20 kg/cm² at 210° C. to 32.5 kg/cm² at 270° C.

6. A plant for the production of methanol by the process according to claim 2, said plant comprising a make-up gas compressor and a synthesis reactor in a methanol loop, wherein a once-through pre-converter is installed between the make-up gas compressor and the methanol loop, said pre-converter operating within the operational window defined by the area below the approximately linear, dashed curve of the partial pressure of carbon monoxide vs. the boiling water temperature for water temperatures from 210 to 270° C., where the partial pressure of carbon monoxide increases from 20 kg/cm² at 210° C. to 32.5 kg/cm² at 270° C.

* * * * *